US008343503B2

(12) United States Patent (10) Patent No.: US 8,343,503 B2
Reymond et al. (45) Date of Patent: Jan. 1, 2013

(54) CONTIGUOUS OVERLAPPING PEPTIDES FOR TREATMENT OF BIRCH POLLEN ALLERGY

(75) Inventors: Christophe Reymond, Prilly (CH); Francois Spertini, Epalinges (CH)

(73) Assignee: Anergis S.A., Epalinges (CH)

( * ) Notice: Subject to any disclaimer, the term of this patent is extended or adjusted under 35 U.S.C. 154(b) by 185 days.

(21) Appl. No.: 12/702,986

(22) Filed: Feb. 9, 2010

(65) Prior Publication Data

US 2010/0203070 A1 Aug. 12, 2010

Related U.S. Application Data

(60) Provisional application No. 61/151,045, filed on Feb. 9, 2009.

(51) Int. Cl.
| | |
|---|---|
| *A61K 38/00* | (2006.01) |
| *A61K 39/00* | (2006.01) |
| *A61K 39/35* | (2006.01) |
| *A61K 39/36* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |

(52) U.S. Cl. .................. 424/185.1; 424/275.1; 514/1.1; 530/300; 530/324

(58) Field of Classification Search ........................ None
See application file for complete search history.

(56) References Cited

U.S. PATENT DOCUMENTS

2005/0249742 A1 11/2005 Ruprecht et al.

FOREIGN PATENT DOCUMENTS

WO WO-2004/081028 A2 9/2004

OTHER PUBLICATIONS

Ngo et al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*
Burgess et al. 'Possible Dissociation of the Heparin-binding and Mitogenis Activities of Heparin-binding (Acidis Fibroblast) Growth Factor-1 from Its Receptor-binding Activites by Site-directed Mutagenesis of a Single Lysine Residue.' J. Cell. Biol. 111:2129-2138, 1990.*
Lazar et al. 'Transforming Growth Factor alpha:Mutation of Aspartic Acid 47 and Leucine 48 Results in Different Biological Activities.' Mol. Cell. Biol. 8(3):1247-1252, 1988.*
Blumenthal et al. 'Definition of an Allergen.' Allergens and Allergen Immunotherapy. Ed. R Lockey, S. Bukantz and J. Bousquet. New York: Marcel Decker, 2004. 37-50.*
Skolnick et al. 'From genes to protein structure and function: novel applications of computational approaches in the genomic era.' Trends in Biotech. 18:34-39, 2000.*
Attwood et al. 'The Babel of Bioinformatics.' Science. 290(5491):471-473.*
Pauli et al., "Comparison of genetically engineered hypoallergenic rBet v 1 derivatives with rBet v 1 wild-type by skin prick and intradermal testing: results obtained in a French population," *Clin. Exp. Allergy*, 30:1076-1084 (2000).
Niederberger et al., "Vaccination with genetically engineered allergens prevents progression of allergic disease," *Colloquium*, 101(2)14677-14682 (2004).
Purohit et al., "Clinical effects of immunotherapy with genetically modified recombinant birch pollen Bet v 1 derivatives," *Clinical and Experimental Allergy*, 38:1514-1525 (2008).
von Gamier et al., "Allergen-derived long peptide immunotherapy down-regulates specific IgE response and protects from anaphylaxis," *Eur. J. Immunol.*, 30:1638-1645 (2000).
Vrtala et al., "Conversion of the Major Birch Pollen Allergen, Bet v 1, into Two Nonanaphylactic T Cell Epitope—containing Fragments," *J. Clin. Invest.*, 99(7): 1673-1681 (1997).
Vrtala et al., "Genetic Engineering of Recombinant Hypoallergenic Oligomers of the Major Birch Pollen Allergen, Bet v 1: Candidates for Specific Immunotherapy," *Int. Arch Allergy Immunol.*, 118:218-219 (1999).
Settipane, R.A., "Demographics and epidemiology of allergic and nonallergic rhinitis," *Allergy Asthma Proc*, 2001. 22(4):85-9.
Bousquet, J., et al., "Assessment of quality of life in patients with perennial allergic rhinitis with the French version of the SF-36 Health Status Questionnaire," *J Allergy Clin Immunol*, 1994. 94(2 Pt 1):182-8.
Son, D.Y., et al., "Pollen-related food allergy: cloning and immunological analysis of isoforms and mutants of Mal d 1, the major apple allergen, and Bet v 1, the major birch pollen allergen," *Eur J Nutr*, 1999. 38(4):201-15.
Jahn-Schmid, B., et al., "Bet v 1142-156 is the dominant T-cell epitope of the major birch pollen allergen and important for cross-reactivity with Bet v 1-related food allergens," *J Allergy Clin Immunol*, 2005. 116(1):213-9.
Breiteneder, H. et al., "A classification of plant food allergens," *J Allergy Clin Immunol*, 2004. 113(5): 821-30.
Drachenberg, K.J., et al., "Single-course specific immunotherapy with mixed pollen allergoids: results of a multi-centre study," *Allergol Immunopathol (Madr)*, 2003. 31(2):77-82.
Petersen K. et al., "Clinical and patient based evaluation of immunotherapy for grass pollen and mite allergy," *Allergol Immunopathol (Madr)*, 2005. 33(5):264-269.
Hartl, A., et al., "Characterization of the protective and therapeutic efficiency of a DNA vaccine encoding the major birch pollen allergen Bet v 1a," *Allergy*, 2004. 59(1):65-73.

(Continued)

*Primary Examiner* — Nora Rooney
(74) *Attorney, Agent, or Firm* — Marshall, Gerstein & Borun LLP

(57) ABSTRACT

Contiguous overlapping peptides (COPs) for the treatment of allergic patients by Specific Immunotherapy (SIT) are provided from the sequence of the major allergen of birch pollen Bet v 1. Such peptides while providing all potential T cell epitopes are devoid of the 3D structure of the original allergen, therefore reducing their ability to bind IgE.

25 Claims, 6 Drawing Sheets

OTHER PUBLICATIONS

Martinez Gomez, J.M., et al., "A protective allergy vaccine based on CpG- and protamine-containing PLGA microparticles," *Pharm Res*, 2007.24(10):1927-35.

Niederberger, V., et al., "Vaccination with genetically engineered allergens prevents progression of allergic disease," *Proc Natl Acad Sci U S A*, 2004. 101 Suppl 2:14677-82.

Pauli, G., et al., "Efficacy of recombinant birch pollen vaccine for the treatment of birch-allergic rhinoconjunctivitis," *J Allergy Clin Immunol*, 2008. 122(5):951-60.

Purohit, A., et al., "Clinical effects of immunotherapy with genetically modified recombinant birch pollen Bet v 1 derivatives," *Clin Exp Allergy*, 2008:1514-1525.

von Garnier, C., et al., "Allergen-derived long peptide immunotherapy down-regulates specific IgE response and protects from anaphylaxis,". *Eur J Immunol*, 2000. 30(6)1 638-45.

Barbey, C., et al., "Intranasal treatment with ovalbumin but not the major T cell epitope ovalbumin 323-339 generates interleukin-10 secreting T cells and results in the induction of allergen systemic tolerance," *Clin Exp Allergy*, 2004. 34(4):654-62.

Hoffmann, A., S. et al., "Biologic allergen assay for in vivo test allergens with an in vitro model of the murine type I reaction," J *Allergy Clin Immunol*, 1997. 99(2):227-32.

Schenk, M.F., et al., "Seven different genes encode a diverse mixture of isoforms of Bet v 1, the major birch pollen allergen," *BMC Genomics*, 2006. 7:168.

Spangfort, M.D., et al., "Three-dimensional structure and epitopes of Bet v 1. Int Arch Allergy," *Immunol*, 1997. 113(1-3):243-5.

Hufnagl, K., et al., "Intranasal tolerance induction with polypeptides derived from 3 noncross-reactive major aeroallergens prevents allergic polysensitization in mice," *J Allergy Clin Immunol*, 2005. 116(2):370-6.

Fellrath et al."Allergen-specific T-cell tolerance induction with allergen-derived long synthetic peptides:Results of a phase 1 trial," 2003 *J. Allergy Clin. Immunol.* 111:854-861.

Birnbaum, J., et al., "Hymenoptera ultra-rush venom immunotherapy (210 min): a safety study and risk factors," *Clin Exp Allergy*, 2003. 33(1):58-64.

Drachenberg, K.J., et al., "Efficacy and tolerability of short-term specific immunotherapy with pollen allergoids adjuvanted by monophosphoryl lipid A (MPL) for children and adolescents," *Allergol Immunopathol (Madr)*, 2003. 31(5):270-7.

\* cited by examiner

Figure 2: Skin Prick Test

A:
C+:Histamine; 1: AllerT1(10μM); 2: AllerT1 (1μM); 3: AllerT1 (0.1μM); 4: AllerT3(10μM); 5: AllerT3 (1μM); 6: AllerT3 (0.1μM); C-: Negative control; 7: AllerT2(10μM); 8: AllerT2 (1μM); 9: AllerT2 (0.1μM); 10: AllerT1-3 (10μM); 11: AllerT1-3 (1μM); 12: AllerT1-3 (0.1μM).
B:
1: rBet v 1 (1μM); 2: rBet v 1 (0.1μM); 3 :rBet v 1 (0.01μM); 4: AllerT4 (10μM); 5: AllerT4 (1μM) 6: AllerT4 (0.1μM); 7: AllerT4-5 (10μM); 8:AllerT4-5 (1μM); 9: Birch (100'000SQ); 10: Birch (10'000SQ); 11: Birch (1000SQ); 12: AllerT5 (10μM); 13: AllerT5 (1μM); 14: AllerT5 (0.1μM); 15:AllerT4-5 (1μM)

Figure 3 Temperature drop induced by the allergen in sensitized mice.
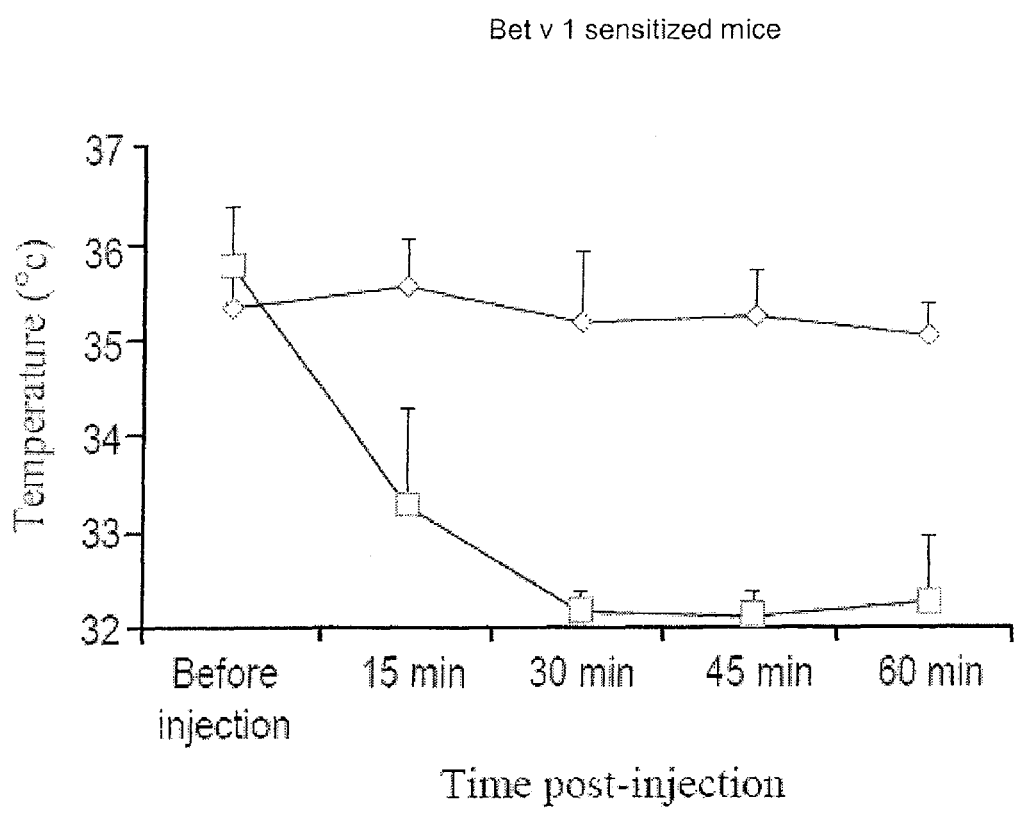
Legend : Squares = Bet v 1; Diamonds = AllerT Figure 4: AllerT does not induce degranulation of basophils
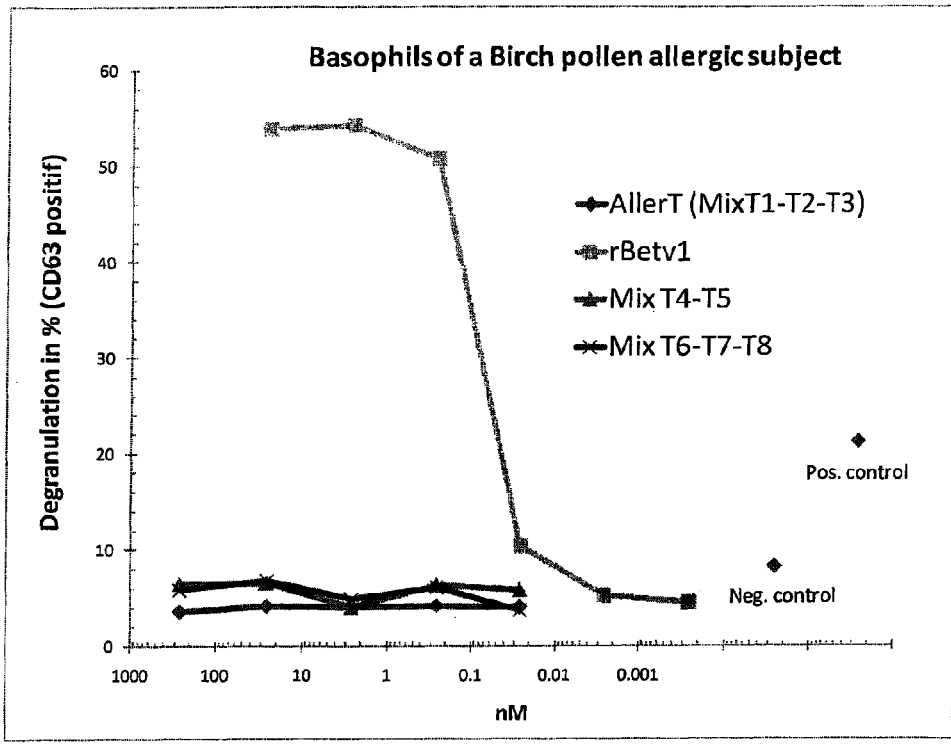
Figure 5 : Induction of IL-10 in allergic subjects treated with AllerT
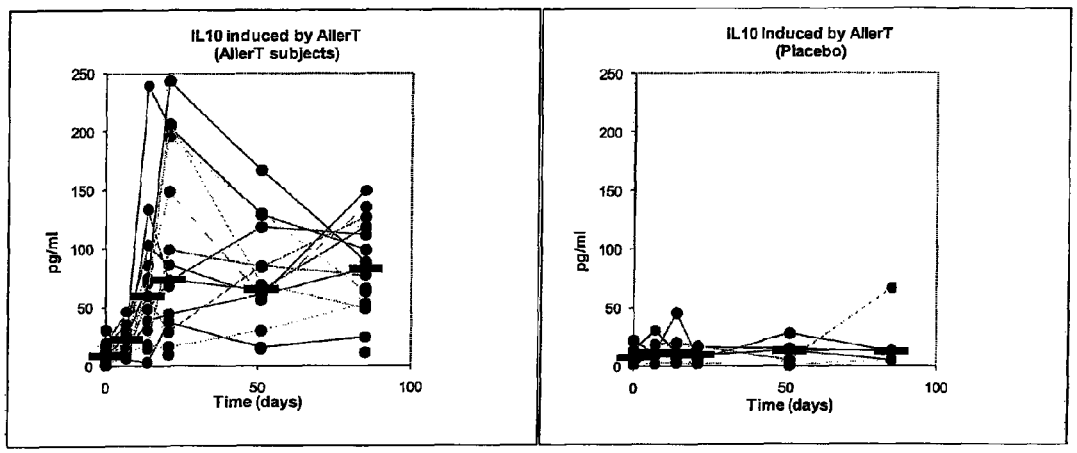

Figure 6: Increase in IgG4 as a result of treatment with AllerT
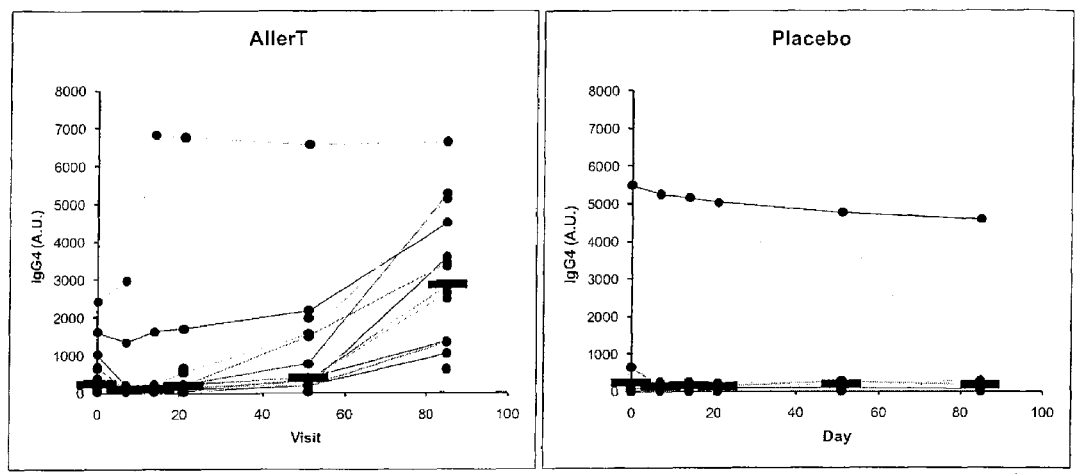

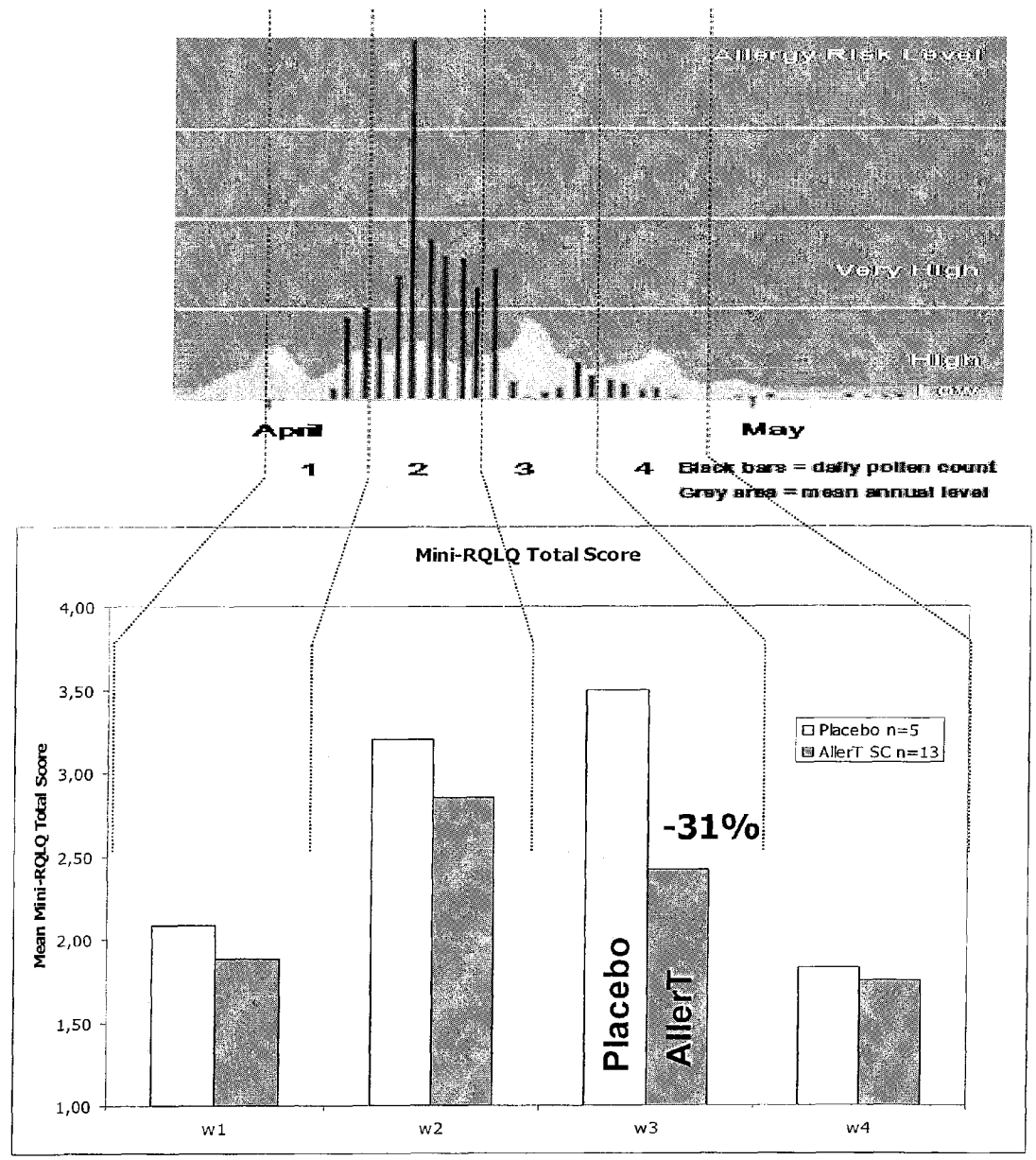
Figure 7: Quality of life during the pollen season after treatment with allerT

CONTIGUOUS OVERLAPPING PEPTIDES FOR TREATMENT OF BIRCH POLLEN ALLERGY

This application claims benefit of U.S. Provisional Application Ser. No. 61/151,045 filed Feb. 9, 2009 the disclosure of which is hereby incorporated by reference.

FIELD OF THE INVENTION

The present invention relates to contiguous overlapping peptides (COPs) derived from the Bet v 1 birch pollen major allergen and the use of such compounds in medicine. The compounds and methods of treatment of the invention are contemplated to be useful in treating birch pollen allergy and widely accelerating its treatment.

BACKGROUND OF THE INVENTION

IgE-mediated allergic disease appears to be very common particularly in industrialized countries where up to one quarter of the population is affected by allergic rhinitis. (Settipane, R. A., *Allergy Asthma Proc*, 22(4):185-9 (2001)). Furthermore people suffering from allergic rhinitis show a lower quality of life than healthy one, (Bousquet, J., et al., *J Allergy Clin Immunol*, 94(2):182-8 (1994)) with only a few going into remission spontaneously. Approximately 25% of all allergic patients respond to tree pollen. Among those, 90% show reactivity with birch pollen extract on cutaneous tests (Skin Prick Tests, SPT). Allergies are triggered by environmental proteins of known peptide sequence and for birch pollen allergy most patients show hypersensitivity to Bet v 1, the major birch pollen allergen. Bet v 1 is part of a protein family playing an important role in plant defense and thus Bet v 1 cross-reacting proteins were found in a number of plants. (Breiteneder, H. et al., *J Allergy Clin Immunol*, 113(5):821-30 (2004)). In addition, allergy to birch pollen is very often related to allergies to other trees of the Fagales family and with certain food allergies, like those to hazel nut, apple, melon and peach. (Son, D. Y. et al., *Eur J Nutr*, 38(4):201-15 (1999) and Jahn-Sclunid et al., *J Allergy Clin Immunol*, 116(1):213-9 (2005)).

The only treatment directed to the cause of IgE-mediated allergy is specific immunotherapy (SIT). The treatment consists in injecting increasing doses of allergens for extended periods of time (three to five years) to induce tolerance in the allergic patient. Several studies showed the benefit of this therapy on the allergic response, in particular upon long-term treatment. (Drachenberg, K. J. et al., *Allergol Immunopathol*, 31(2):77-82 (2003) and Dam Petersen, K. et al., *Allergol Immunopathol* 33(5)264-269 (2005)). However, a number of side effects were observed particularly during ultra rush therapies, where up to 30% of the patients have to be treated for allergic symptoms during the course of therapy. (Birnbaum et al., *Clin. Exp. Allergy*, 33(1):58-64 (2003)). There is thus a strong medical need for an alternative to SIT in the form of a shorter treatment with acceptable safety.

Different approaches have been tested to improve the safety and efficacy of SIT. Formulations or existing extracts have been improved by adding adjuvants, like MPL (Allergy Therapeutics), (Drachenberg, K. J. et al., *Allergol Immunopathol*, 31(5):270-7 (2003)) DNA sequences (Hartl, A. et al., *Allergy*, 59(1):65-73 (2004)) or bacteriophage combined with CpG (Martinez Gomez, J. M. et al., *Pharm. Res.*, 24(10): 1927-35 (2007)) which increase the TH1 immune response, thus allowing possible reductions in the amount of allergen extract. Defined allergens were used instead of whole extracts. In the case of birch pollen, a clinical trial with recombinant Bet v 1 has shown efficacy equivalent to whole birch pollen extract (Pauli, G. et al., *J. Allergy Clin. Immunol*, 122(5):951-60 (2008)).

To diminish the occurrence of allergic symptoms resulting from treatment, different groups explored the use of products with hypoallergenic potential, namely showing reduced IgE binding. In particular, peptides encompassing a restricted number of T-cell epitopes were used for allergen immunotherapy of cat dander with limited efficacy (Campbell, J D et al., *J Exp Med.*, 206(7):1535-47 (2009)). However, allergens harbor a great variety of T cell epitopes partly dependent on the HLA type of the patient. For example, T cell epitopes were found scattered throughout the Bet v 1 sequence, except for a short region (Jahn-Schmid B. et al., *J Allergy Clin Immunol*, 116(1):213-9 (2005)). Thus an efficient immunotherapy product should preferably contain the complete sequence of the allergen rather than selected T-cell epitopes.

The use of fragments of allergens remains attractive, based on the evidence that human IgE recognize mainly non-contiguous epitopes which may be separated by fragmentation of the allergen. Two contiguous fragments of Bet v 1 or trimeric forms of Bet v 1 were tested in a phase I study in human and showed a trend towards improvement of well being but provided no significant improvement in symptom medication scores (Niederberger, V. et al., *Proc Natl Acad Sci USA*, 101(2):14677-82 (2004)). In that study, however, a number of adverse events were observed, the majority of which occurred hours after the injections (Purohit, A. et al, *Clin Exp Allergy* (2008)). Three fragments of the major allergen of bee venom, namely phospholipase A2, were also tested in human, showing an excellent safety due to lowered IgE binding while eliciting elevated levels of IgG4 and IL-10 (Fellrath et al., *J. Allergy Clin. Immunol*, 111:854-861 (2003)). A method was devised to select contiguous overlapping peptides (COPs) for treatment of allergy which together form the entire amino acid sequence of an allergen, thus providing all possible T cell epitopes of the allergen, while having lowered IgE binding (Patent application WO2004/081028 A2). Such selected fragments show a reduced ability to reform the original tertiary structure of the allergen, if any, resulting in a reduced ability to bind IgE and therefore to elicit allergic reactions in humans.

SUMMARY OF THE INVENTION

According to one aspect, the present invention provides contiguous overlapping peptides (COPs) as a composition for the treatment of birch pollen allergies. Specifically, COPS are provided from the sequence of the major allergen of birch pollen Bet v 1 which provide all potential T cell epitopes but are devoid of the three dimensional structure of the original allergen, therefore potentially reducing their ability to bind IgE.

According to a further aspect, the invention relates to a specific immunotherapy (SIT) method able to reduce allergic symptoms after a few administrations over a short period of time. This therapy consists of repeatedly administering specific COPs to humans suffering from birch pollen allergy. Administration may be done by systemic, transdermal, intradermal subcutaneous, or by oral routes, or mucosal routes including sublingual and intestinal routes. Administration may in some embodiments be repeated five times over two month compared to 3 to 5 years for current SIT. Administered amount of active product (COPs) may reach a cumulated value equivalent in molar amount to the amount of Bet v 1 administered over three year of SIT treatment.

Specifically the invention provides a composition comprising a plurality of contiguous overlapping peptide fragments comprising a first peptide comprising the sequence from amino acid 2 to amino acids 42-52 of SEQ ID NO: 9 wherein the reactivity of said peptide to IgE antibodies of subjects who are allergic to birch pollen is eliminated while the reactivity with the T lymphocytes from subjects who are allergic to birch pollen is retained; a second polypeptide comprising the sequence from amino acids 42-52 to amino acids 96-131 of SEQ ID NO: 9 wherein the reactivity of said peptide to IgE antibodies of subjects who are allergic to birch pollen is eliminated while the reactivity with the T lymphocytes from subjects who are allergic to birch pollen is retained and a third peptide comprising the sequence from amino acids 96-131 to amino acid 160 of SEQ ID NO: 9 wherein the reactivity of said peptide to IgE antibodies of subjects who are allergic to birch pollen is eliminated while the reactivity with the T lymphocytes from subjects who are allergic to birch pollen is retained. According to a preferred aspect of the invention, the first and second peptides overlap each other by 1 to 11 amino acids. According to another preferred aspect of the invention the second and third peptides overlap each other by 5 to 20 amino acids. Particularly preferred compositions comprise the combination of the peptide having SEQ ID NO: 1, the peptide having SEQ ID NO:2 and the peptide having SEQ ID NO: 3 or the combination of the peptide having SEQ ID NO: 6, the peptide having SEQ ID NO: 7 and the peptide having SEQ ID NO: 8.

Preferred COP compositions include those wherein the peptides are capable upon administration in humans of inducing a 10 fold increase in IgG4 antibodies specific to birch pollen allergen Bet v 1 over the level of IgG4 present before treatment in a panel of at least 15 individuals sensitive to birch pollen. Other preferred compositions are characterized in that the peptides are capable upon administration in humans of inducing an over a 5 fold increase in IL-10 to birch pollen allergen Bet v 1 over the level of IL-10 present before treatment in a panel of at least 15 individuals sensitive to birch pollen.

Also provided are peptides comprising the sequence from amino acid 2 to amino acids 42-52 of SEQ ID NO: 9 and peptides having 90% and 80% and 70% sequence identity thereto wherein the reactivity of said peptide to IgE antibodies of subjects who are allergic to birch pollen is eliminated while the reactivity with the T lymphocytes from subjects who are allergic to birch pollen is retained. Particularly preferred are peptides which have the sequence of SEQ ID NO: 1 or of SEQ ID NO 6.

Also provided are peptides comprising the sequence from amino acids 42-52 to amino acids 96-131 of SEQ ID NO: 9 and peptides having 90% and 80% and 70% sequence identity thereto wherein the reactivity of said peptide to IgE antibodies of subjects who are allergic to birch pollen is eliminated while the reactivity with the T lymphocytes from subjects who are allergic to birch pollen is retained. Particularly preferred are peptides which have the sequence of SEQ ID NO: 2 or of SEQ ID NO 7.

Also provided are peptides comprising the sequence from amino acids 96-131 to amino acid 160 of SEQ ID NO: 9 and peptides having 90% and 80% and 70% sequence identity thereto wherein the reactivity of said peptide to IgE antibodies of subjects who are allergic to birch pollen is eliminated while the reactivity with the T lymphocytes from subjects who are allergic to birch pollen is retained. Particularly preferred are peptides which have the sequence of SEQ ID NO: 3 or of SEQ ID NO 8.

Such peptides can be obtained by any of a variety of methods including by chemical synthesis or by recombinant means.

The COPs and peptides of the invention can be provided in dry powdered form but can also be provided in combination with an acceptable carrier or diluent. In addition, the compositions can further comprise an adjuvant with a preferred adjuvant being aluminium hydroxide. As such the compositions can be characterized as and used as a vaccine composition.

Also provided are methods of specific immunotherapy (SIT) against birch pollen allergies comprising administering to a patient in need thereof one or more allergens selected from the group consisting of a first peptide comprising the sequence from amino acid 2 to amino acids 42-52 of SEQ ID NO: 9 wherein the reactivity of said peptide to IgE antibodies of subjects who are allergic to birch pollen is eliminated while the reactivity with the T lymphocytes from subjects who are allergic to birch pollen is retained; a second polypeptide comprising the sequence from amino acids 42-52 to amino acids 96-131 of SEQ ID NO: 9 wherein the reactivity of said peptide to IgE antibodies of subjects who are allergic to birch pollen is eliminated while the reactivity with the T lymphocytes from subjects who are allergic to birch pollen is retained and a third peptide comprising the sequence from amino acids 96-131 to amino acid 160 of SEQ ID NO: 9 wherein the reactivity of said peptide to IgE antibodies of subjects who are allergic to birch pollen is eliminated while the reactivity with the T lymphocytes from subjects who are allergic to birch pollen is retained.

Such methods can be carried out in which the peptides are administered using intradermal injection, subcutaneous injection, intramuscular injection, intravenous injection, transdermal, intranasal, oral, sublingual, intraocular, or intrathecal techniques.

According to one such method, a patient is treated with the combination of each of a first peptide comprising the sequence from amino acid 2 to amino acids 42-52 of SEQ ID NO: 9 wherein the reactivity of said peptide to IgE antibodies of subjects who are allergic to birch pollen is eliminated while the reactivity with the T lymphocytes from subjects who are allergic to birch pollen is retained; a second peptide comprising the sequence from amino acids 42-52 to amino acids 96-131 of SEQ ID NO: 9 wherein the reactivity of said peptide to IgE antibodies of subjects who are allergic to birch pollen is eliminated while the reactivity with the T lymphocytes from subjects who are allergic to birch pollen is retained and a third peptide comprising the sequence from amino acids 96-131 to amino acid 160 of SEQ ID NO: 9 wherein the reactivity of said peptide to IgE antibodies of subjects who are allergic to birch pollen is eliminated while the reactivity with the T lymphocytes from subjects who are allergic to birch pollen is retained. According to one preferred method the first and second peptides overlap each other by at least 1 to 11 amino acids while the second and third peptides overlap each other by at least 5-20 amino acids. According to another preferred embodiment the first peptide consists of SEQ ID NO: 1, the second peptide consists of SEQ ID NO:2 and the third peptide consists of SEQ ID NO: 3 and according to another preferred embodiment the first peptide consists of SEQ ID NO: 6, the second peptide consists of SEQ ID NO:7 and the third peptide consists of SEQ ID NO: 8.

BRIEF DESCRIPTION OF THE DRAWINGS

FIG. 3 depicts the temperature levels of mice injected with the birch pollen allergen. A large amount of r Bet v 1 was injected in the sensitized mice (filled squares) resulting in temperature drop within 30 minutes. The selected COPs (T1, T2 and T3) forming the product AllerT (open diamonds) do not induce a temperature drop in sensitized mice.

FIG. 4 depicts the ability of r Bet v 1 to induce basophil degranulation in a Basotest® assay. COPs do not induce basophil degranulation at any tested concentration.

FIG. 5 depicts the increase in IL-10 in PBMCs during and up to one month post treatment. Horizontal bars represent mean values of the results from the individual subjects (dots).

FIG. 6 depicts the increase in IgG4 in the sera of subjects treated with AllerT or a placebo during and up to one month post treatment. Horizontal bars represent mean values of the results from the individual subjects (dots).

FIG. 7 depicts the pollen season 2009 in the Lausanne area in correlation with the mean scores of a mini Rhino-conjunctivitis Quality of Life Questionnaire. (RQLQ, Juniper, E. F., et al., *Clin. Exp. Allergy*, 30: 132-140 (2000)).

DETAILED DESCRIPTION OF THE INVENTION

Figure 1A:
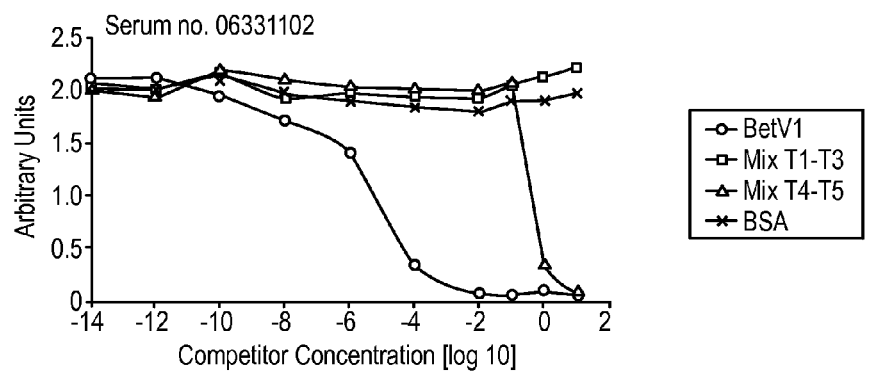
FIG. 1 depicts the competitive binding of selected COPs to IgE compared to Bet v 1. COPs either in combination (panels A and D) or individually (panels B and C) were pre-incubated with serum from birch pollen allergic subjects. Residual Bet v 1 specific IgE was monitored using ELISA plates coated with r Bet v 1.
Figure 1B:
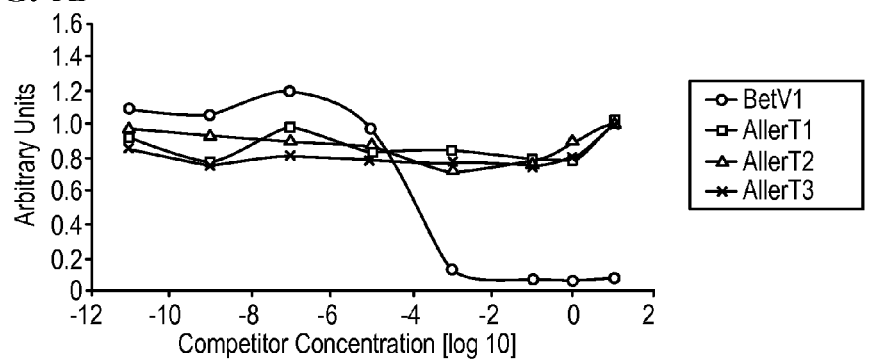
Figure 1C:
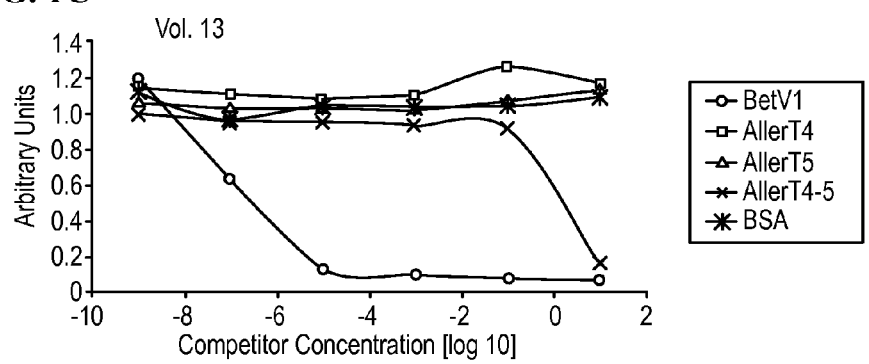

The invention is described below by way of examples with reference to the following experimental procedures and results.

In order to select for products with lowered IgE binding, three sets of long (30-90 amino acids) contiguous overlapping peptides (COP) were devised encompassing the entire Bet v I allergen, thus providing all possible T cell epitopes. A first set encompassed three peptides AllerT1, -T2 and -T3 with reduced ability to form secondary structures as derived from analysis based on potential IgE epitopes and the tertiary structure of Bet v 1. A second set of three COPs, AllerT6, -T7 and -T8, was selected. A third set contained two COPs, AllerT4-T5, approximately splitting the allergen in two parts irrespective of IgE epitopes and tertiary structure. The first and second sets of peptides were tested through a combination of in vitro IgE competition tests and skin prick tests in human. The absence of reactivity with Bet v I was further tested using mice sensitized with Bet v 1 as well as through degranulation of human basophils. The first set, named AllerT, was further used in humans to treat birch pollen allergic subjects.

Material and Methods
Allergens

Purified recombinant Bet v 1 was purchased from BIOMAY (Vienna, Austria). Birch pollen extract, Aquagel SQ (ALK Wassrig SQ), was obtained from ALK Abello, Hosshom, Denmark.

Choice of Peptides and Synthesis

The aim was to prevent the formation of stable tertiary structures of B cell epitope, while presenting all T cell epitopes present within the Bet v 1 sequence. As a result, the following first set of COPs which overlap along the Bet v 1 sequence were selected, namely:

```
SEQ ID NO: 1
AllerT1: aa 2-50 of SEQ ID 9
GVFNYETETT SVIPAARLFK AFILDGDNLF PKVAPQAISS
VENIEGNGG
Theoretical pI/Mw: 4.36/5198.82

SEQ ID NO: 2
AllerT2: aa 48-118 of SEQ ID 9
NGGP GTIKKISFPE GFPPKYVKDR VDEVDHTNFK YNYSVIEGGP
IGDTLEKISN EIKIVATPDG GSILKIS
Theoretical pI/Mw: 5.72/7742.76

SEQ ID NO: 3
AllerT3: aa 106-160 of SEQ ID 9
VATPDG GSILKISNKY HTKGDHEVKA EQVKASKEMG ETLLRAVESY
LLAHSDAYN
Theoretical pI/Mw: 6.29/6001.72

SEQ ID NO: 4
Aller T4: aa 2-85 of SEQ ID 9
GVFNYETETT SVIPAARLFK AFILDGDNLF PKVAPQAISS
VENIEGNGGP GTIKKISFPE GFPPKYVKDR VDEVDHTNFK YNYS
Theoretical pI/Mw: 5.24/9348.49

SEQ ID NO: 5
AllerT5: aa 65-160 of SEQ ID 9
FKYVKDR VDEVDHTNFK YNYSVIEGGP IGDTLEKISN
EIKIVATPDG GSILKISNKY HTKGDHEVKA EQVKASKEMG
ETLLRAVESY LLAHSDAYN
Theoretical pI/Mw: 5.77/10759.06

SEQ ID NO: 6
AllerT6 aa 2-49 of SEQ ID 9
GVFNYETETT SVIPAARLFK AFILDGDNLF PKVAPQAISS
VENIEGNG
Theoretical pI/Mw: 4.36/5141.77

SEQ ID NO: 7
AllerT7 aa 44-118 of SEQ ID 9
NIEGNGG PGTIKKISFP EGFPFKYVKD RVDEVDHTNF
KYNYSVIEGG PIGDTLEKIS NEIKIVATPD GGSILKIS
Theoretical pI/Mw: 5.24/8156.19

SEQ ID NO: 8
AllerT8 aa 103-160 of SEQ ID 9
IKIVATPD GGSILKISNK YHTKGDHEVK AEQVKASKEM
GETLLRAVES YLLAHSDAYN
Theoretical pI/Mw: 7.03/6356.22

SEQ ID 9:
Bet v 1 sequence as published under Swissprot
P15494
MGVFNYETET TSVIPAARLF KAFILDGDNL FPKVAPQAIS
SVENIEGNGG PGTIKKISFP EGFPFKYVKD RVDEVDHTNF
KYNYSVIEGG PIGDTLEKIS NEIKIVATPD GGSILKISNK
YHTKGDHEVK AEQVKASKEM GETLLRAVES YLLAHSDAYN
```

All eight COPs were synthesized by solid phase fmoc chemistry at research scale to allow determination of IgE binding and first animal tests. Preparative HPLC was used to obtain over 90% pure peptides which were lyophilized. Peptides were resuspended in water at 2 mg/ml and frozen in aliquots.

Competition ELISA

Recombinant Bet v 1 at 0.5 μg/ml (r Bet v 1 obtained from Biomay, Austria) was coated overnight on 96-well Nunc Maxisorp® immunoplates (Life Technologies, Basel, Switzerland). After blocking with 1% BSA, ten-fold dilutions of patient serum were added. Rat anti-mouse mAb IgE at 2 μg/ml (PharMingen, BD-Biosciences, San Diego, Calif.) were then added and antibodies were revealed with extravidin-coupled alkaline phosphatase (Sigma Diagnostic Inc., St-Louis, Mo., USA). The sera of three allergic patients were selected for high IgE level and clear signal over background and used to test for competition with the peptides. Serial dilutions of each COP, namely AllerT1, AllerT2, AllerT3, AllerT4, AllerT5, AllerT6, AllerT7 and AllerT8, or mixtures of AllerT1-3, AllerT4-5 and AllerT6-8, starting at 10 μM, were pre-incubated with the three selected sera overnight at 4° C. Sera were then incubated on r Bet v 1 coated 96-well plates and residual IgE binding was determined as described above. r Bet v 1 dilutions were used as control for inhibition, whereas BSA was used as control for possible non-specific inhibition.

Animals

Four weeks-old female BALB/c mice (H-2d) were obtained from Harlan (AD Horst, The Netherlands) and used at the age of 6-8 weeks. They were maintained under standard housing conditions on ovalbumin (OVA)-free diet and water ad libitum.

Immunization Protocol

Mice were sensitized by sub-cutaneous (s.c.) injections of indicated concentrations of r Bet v 1 (Biomay) adsorbed on 2 mg Alum (Sigma Chemicals, St-Louis, Mo., USA) at indicated intervals. Injections were done in the abdomen and at the basis of the tail of the mice Antibody Isotypes in Mice Kinetics of serum IgE, IgG 1 and IgG 2a antibody response was determined by ELISA as described. (von Gamier, C, et al., *Eur J Immunol*, 30(6):1638-45 (2000) and Barbey, C. et al., *Clin Exp Allergy*, 34(4):65462 (2004)). Briefly, 96-well Nunc Maxisorp® immunoplates (Life Technologies, Basel, Switzerland) were coated with 5 mg/ml r Bet v 1. After blocking with 1% BSA, optimal dilutions of mouse serum were added, namely 1:5 for IgE, 1:500,000 for IgG 1, 1:1,000 for IgG 2a respectively. Rat anti-mouse mAb IgE at 2 mg/ml (PharMingen, BD Biosciences, San Diego, Calif.); or purified polyclonal goat anti-mouse IgG 1 diluted 1:3000 (Caltag, WBAG Resources, Zurich, Switzerland); or purified polyclonal goat anti-mouse IgG 2a diluted 1:3000 (Caltag) were added as secondary antibodies and revealed with alkaline phosphatase (Sigma Diagnostic Inc., St-Louis, Mo., USA). For IgE isotypes, purified mouse IgE (27-74, PharMingen) was used as standard in microwells coated with rat anti-mouse IgE (R35-72, PharMingen) al 2 mg/ml. Results were expressed in ng/ml as arbitrary units.

Basophil Degranulation Tests

Basotest® (ORPEGEN Pharma Heidelberg, Germany) was used for the quantitative determination of in vitro basophile degranulation. Heparinized blood (100 μl) from a birch pollen allergic donor was first incubated with a stimulation buffer for 20 min at 37° C., and then with or without chemotactic peptide formylmethionylleucylphenylalanine (fMLP) as positive and negative controls respectively. Aliquots of blood were incubated in parallel with 100 μl allergen solution diluted in a saline solution for 20 min at 37° C. A dose response curve was performed with 25, 2.5, 0.25, 0.025 and 0.0025 nano-molar r Bet v 1 as well as starting 10 fold higher with AllerT mixes (AllerT1-T3, AllerT4-5 and AllerT6-8). The activation process was stopped by incubating the blood samples at 4° C. for 10 min. The samples were then incubated for 20 min at +4° C. with 20 μl of phycoerythrin (PE)-conjugated anti-IgE and fluorescein isothyocyanate (FITC)-conjugated anti-gp53 (CD63). Erythrocytes were subsequently removed by the addition of 2 ml of lysing solution (Becton-Dickinson). Cells were washed twice with PBS solution and resuspended in 200 μl of PBS solution and analyzed within 1 h by cytofluorimetry (FASCalibur, BectonDickinson). The basophile population was gated on the PE anti-IgE positive cells and the expression of gp53 (CD63) was analyzed on this population. Acquisition was performed on 1,000 cells for each sample and results are given as the percentage of basophils (IgE-positive cells) expressing gp53 (CD63). Positive degranulation was set at a cutoff of 15% IgE-positive cells expressing CD63 according to the Basotest® notice.

Skin Prick Testing of Allergic Patients

Twenty volunteers suffering from seasonal rhino-conjunctivitis or asthma during the period of birch pollinosis were selected, including seven males and thirteen females with a mean age was 30.1 years (range 23-45 years). All subjects reacted to birch pollen extracts (Aquagen SQ), and to r Bet v 1 (Biomay) by standard skin prick tests (SPT). Serological reactivity (IgE antibodies) was also positive for birch pollen and Bet v 1 as determined by CAP-RAST. The allergenic response of the peptides was evaluated in vivo by SPT with each of the 5 peptides (AllerT1, AllerT2, AllerT3, AllerT4 and AllerT5) and with the 2 sets (AllerT1-3 and AllerT4-5) on all patients. For each peptide, a 20 μl drop was applied on the forearm at 3 different concentrations (10, 1 and 0.1 μM). Birch pollen extract (Aquagen SQ, ALKAbello) and Bet v 1 (Biomay) were also tested with SPT at 3 concentrations 10 times lower than the one used for peptides namely 100,000, 10,000 and 1,000 SQ for birch pollen as well as 1, 0.1 and 0.01 μM for Bet v 1. The weal diameter was evaluated by taking the maximal diameter. SPT was considered positive when the weal diameter was 4 mm or more with an erythema (Hoffmann, A. et al., *J Allergy Clin Immunol*, 99(2):227-32 (1997). Reactions resulting in a weal diameter below 4 mm, while exceeding 2 mm, were also recorded and classified as "dubious".

Experimental Results

Choice of Peptides

Bet v 1 is a mature protein of 159 amino acids after removal of the first methionine (NCBI X15877, Swissprot P15494) and is present in different isoforms on the birch pollen grains (Schenk, M. F. et al., *BMC Genomics*, 7:168 (2006)). In addition, the Bet v 1 family shows sequence homology with some food allergens like celery (NCBI: Structure 1BTV, 1FM4_A, 2BKO_A). A strong allergic cross reaction has been documented between Fagales species (birch, hazel, alder and hornbeam). Bet v 1 sequence comparison between these species showed regions of particularly high sequence conservation which represent candidates for being the B cell epitopes responsible for the allergic reaction as proposed by Spangfort et al. (Spangfort, M. D. et al., *Int Arch Allergy Immunol*, 113(1-3):243-5 (1997)). Three regions from SEQ ID 9 can be proposed to hind to IgE, namely a first region, epitope B1, from amino acid (aa) 97-122 combined with aa 132-142; a second region, epitope B2, encompassing aa 16-24 combined with aa 143-155; and a third region, epitope B3 containing the loop with homology to the GTP binding sequence GXGXXG (SEQ ID NO: 10) located at aa 42-53. On the other hand, T cell epitopes are scattered throughout the Bet v 1 sequence except for amino acids 49-60, containing the potential GTP binding site GXGXXG (SEQ ID NO: 10).

Potential epitopes can be predicted using epitope computer predictive tools as proposed in the Immune epitope and database and analysis resource (IEDB) (http://immuneepitope.org/). In particular, ElliPro predicts linear and discontinuous antibody epitopes based on a protein antigen's 3D structure. Within the linear epitopes predicted by ElliPro, one potential epitope was found to match with the epitope B3 (loop 41-52) predicted by Spangfort et al. Three discontinuous epitopes were predicted by ElliPro which differed from those proposed by Spangfort et al. 1997. The first one includes aa 1-4 combined with aa 123-126; the second included aa92-95 with amino acid 127; the third includes aa10-15 with aa106-114.

Combining knowledge about the mature protein missing the first residue and the prediction of a potential linear epitope between amino acids 42 to 53, the first COP has to start at amino acid 2 and end between aa 42 and 52. The second COP has to start between amino acids 42 and 52, in order to prevent the formation of the original linear epitope, and may have an overlap to the first COP. The extent of the overlap is determined by the fact that no T cell epitope was found within the region of aa 49-60. Thus the overlap can range from a minimum of 0 if the end of the first COP is between amino acids 49 and 53 up to a maximum of 11 if the end of the first COP is between aa 42 and 48. The end of the second COP has to be placed between aa 96 and 131 to prevent the formation of epitope B1 as well as the second epitope predicted by ElliPro cited above. The start of the third COP has to be located between aa 96 and 131 for the reasons cited above to prevent B cell epitope formation. Overlaps can range from 5 to 20 amino acids to provide all possible T cell epitopes.

Based on the sequence P15494 (Swissprot), used by others in recombinant form for clinical trials (Pauli, G. et al., *J Allergy Clin Immunol*, 122(5):951-60 (2008)), and the predictions above, three sets of peptides were devised encompassing the complete Bet v 1 sequence. The sets AllerT1, -T2 and -T3 (SEQ ID NO: 1, 2 and 3 respectively) as well as AllerT6, -T7 and -T8 (SEQ ID NO 6, 7 and 8 respectively), were devised according to the rule described above, namely possess ending points and overlaps preventing formation of predicted discontinuous B cell epitopes. In particular the peptides were overlapped at their extremities by 3 and 13 amino acids between AllerT1-AllerT2 and AllerT2-AllerT3 respectively. Overlaps are of 6 and 16 amino acids respectively between AllerT6-AllerT7 and AllerT7-AllerT8 respectively. Another set of COPs, namely AllerT4-T5 was chosen without taking the above predictions into account and is composed of only two peptides which overlap by 21 amino acids. The epitopes B1 and B3, previously mentioned, are fully present on AllerT5 and AllerT4 respectively, whereas the second discontinuous epitope predicted by ElliPro is present on AllerT5. All contiguous overlapping peptides (COPs) were either used separately or mixed in equimolar amounts in further experiments.

IgE Binding of Selected COPs Compared to r Bet v 1

Figure 1D:
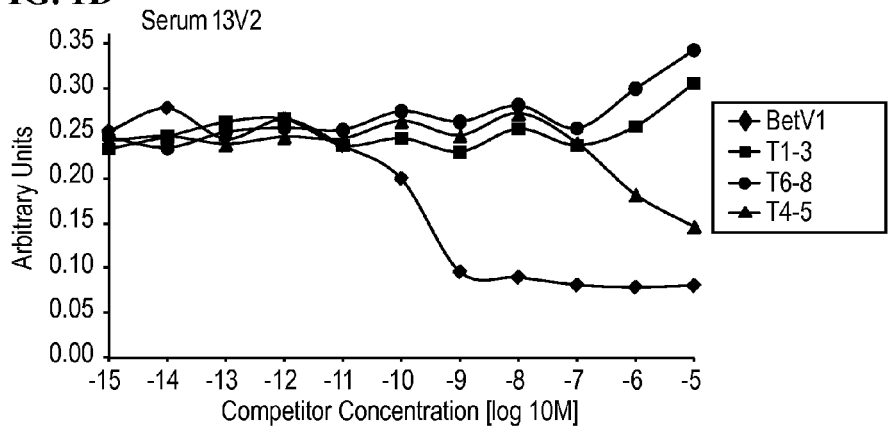

COPs were first tested in vitro for reduced IgE binding by competition ELISA as described in material and methods. As seen in FIG. 1, r Bet v 1 competed with IgE present in the sera at concentrations ranging from $10^{-10}$ to $10^{-5}$ M (50% inhibition) depending on the serum of the donor, whereas BSA showed no detectable inhibition at all concentrations tested. Aller T1, T2 and T3 either alone (FIG. 1B) or in equimolar combination (FIG. 1A) showed no competition. The same result was obtained with peptides selected according to the same rules, namely AllerT6, T7 and T8 (FIG. 1D). Aller T4 and T5 alone showed a comparable result (FIG. 1C), whereas, surprisingly, the combination of Aller T4 with Aller T5 showed some inhibition, albeit at least at 1,000 fold higher concentration than r Bet v 1 (FIGS. 1 A and C). Competition assays were performed with sera from three allergic patients, confirming the absence of competition of the combined sets AllerT1, T2 and T3 as well as AllerT6, T7 and T8 with Bet v 1 for IgE binding (data not shown).

Effect of Selected COPs in Mice Sensitized to Bet v 1

A first series of mice were treated according to the protocol developed by Hufnagl, K. et al., *J Allergy Clin Immunol*, 116(2):370-6 (2005), namely by three intraperitoneal (i.p.) injections and were challenged by tree pollen aerosol. In our hands, IgE against Bet v 1 was undetectable after the injection period, indicating that the mice were not sensitized. Accordingly, tree pollen challenge failed to increase the presence of eosinophils in bronchial lavage fluid (data not shown). We thus applied the sensitization protocol used in previous murine studies for bee venom PLA2 (von Garnier, C. et al., *Eur J Immunol*, 30(6):1638-45 (2000)). Mice were sensitized by six subcutaneous injections of r Bet v 1 in Aluminium hydroxide at 2 weeks intervals. Concentrations ranging from 0.1 to 10 µg were tested. Interestingly Bet v 1 specific IgE increased significantly only after the fourth injection in mice sensitized with 0.1 µg, possibly explaining why the previous experiment failed. IgG2 levels (corresponding to protective IgG4 in human) started to increase after the $4^{th}$ injection and steadily increased thereafter, showing a maximum after 6 injections. IgG2a specific to Bet v 1 seemed to increase slightly later than IgE specific levels.

The sensitization of mice was tested by injecting i.p. a high dose (30 µg) of r Bet v I and recording rectal temperature. As seen in FIG. 3, a temperature drop was observed within 30 minutes after injection of r Bet v 1 showing a strong systemic allergic response. Injection of 150 µg of AllerT did not lead to a temperature shift, thus indicating an increased safety of the COP based approach over r Bet v 1 at least in animal. No significant difference was observed between mice sensitized with 0.1, 1.0 or 10 µg of r Bet v 1 (data not shown). Thus, mice sensitized to r Bet v 1 did not show a temperature decrease when challenged with AllerT, a test resembling anaphylactic shock in human.

Basophil Degranulation Tests

In order to further verify the safety of AllerT, the COPs were tested in a basophil degranulation assay (Basotest®). Basophils degranulated when stimulated with r Bet v 1 in a concentration dependent manner (FIG. 4). On the contrary, individual COPs (AllerT1 to AllerT8) and combinations were unable to induce degranulation above the level observed with a negative control. No degranulation was observed through a range of COPs concentrations up to 1,000 fold that of the Bet v 1 concentration able to induce half maximal degranulation (FIG. 4). The absence of degranulation of basophils indicates a potentially diminished risk of immediate allergic reaction upon application in human.

Skin Prick Tests (SPT)

Figure 2:
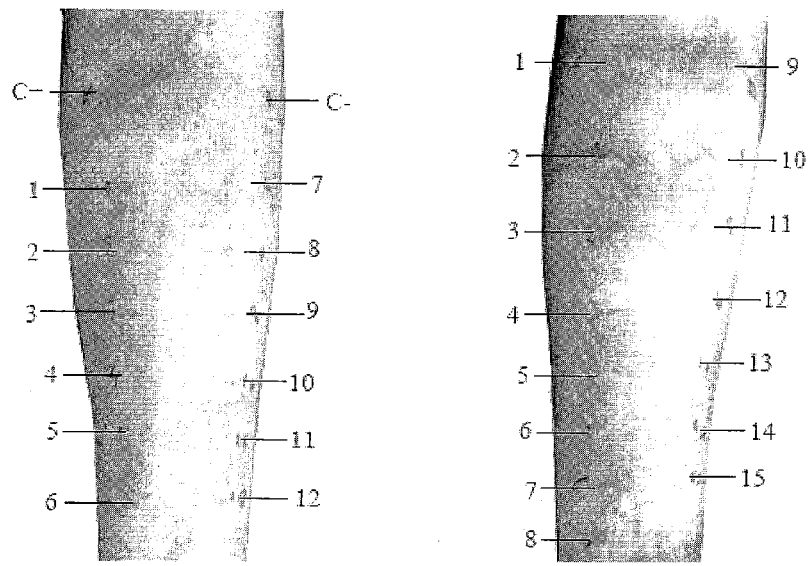
FIG. 2 depicts the right and left arms of a birch pollen allergic subject described in the Skin prick tests (SPT) section. SPT were performed with various COPs and their combinations. Histamine was used as positive control. Birch pollen and equivalent amounts of r Bet v 1 were tested at three concentrations, whereas COPs were tested in parallel up to a 10 fold higher concentration.

SPT with the AllerT COPs were performed on 20 volunteers presenting allergic rhinitis symptoms confirmed by either a positive CAP RAST and/or positive skin reaction to birch pollen (Table I). As expected, SPT were positive in all volunteers with either birch pollen extracts or recombinant Bet v 1 at concentrations of 100,000 SQ and 1 µM respectively (Table II A). At lower concentrations, 80 to 85% of the subjects showed positive reaction to a 10 fold dilution, whereas 5 to 10% of the subjects showed reactivity to a 100 fold dilution of birch pollen or r Bet v 1. Concentrations of the peptides as high as 10 fold over r Bet v 1 were tested (up to 10 µM). None of the COPs showed positive skin reactions above the defined threshold, namely a weal diameter over 4 mm with erythema (example of arms from one subject in FIG. 2).

TABLE I

Characteristics of subjects

| | Subjects |
|---|---|
| Number of subjects | 20 |
| Mean age (range) | 30.1 years (23-45) |
| Males/females | 7/13 |
| Asthma | 7 |
| Rhinitis | 20 |
| Peak flow (% predicted value) | 93.75 L/min (61-117) |

TABLE I-continued

Characteristics of subjects

| | Subjects |
|---|---|
| IgE birch (kU/L) (range) | 29.34 (0.7-100) |
| IgE Bet v 1 (kU/L) (range) | 29.48 (0.35-100) |

TABLE II. A

Skin prick test results
Positive skin reactions:

| | Dilutions | | |
|---|---|---|---|
| | 1:1 | 1:10 | 1:100 |
| Birch (10'000 SQ) | 20 | 17 | 1 |
| r Bet v 1 (1 µM) | 20 | 16 | 2 |
| AllerT1 (10 µM) | 0 | 0 | 0 |
| AllerT2 (10 µM) | 0 | 0 | 0 |
| AllerT3 (10 µM) | 0 | 0 | 0 |
| Mix AllerT1-3 (10 µM) | 0 | 0 | 0 |
| AllerT4 (10 µM) | 0 | 0 | 0 |
| AllerT5 (10 µM) | 0 | 0 | 0 |
| Mix AllerT4-5 (10 µM) | 0 | 0 | 0 |

Skin reactions below the defined threshold were occasionally observed in some subjects. Such dubious reactions were scored when observing a detectable weal edema below 4 mm with or without erithema (Table II B). Such reactions were observed with low concentration of either birch pollen or r Bet v 1 (data not show). Prick tests may elicit local irritations independent of the products in some subjects. Indeed, one reaction lower than defined threshold was scored sporadically in one or the other volunteer. Assuming such reactions as background, statistical precaution leads to define dubious reactions in over three subjects as possibly significant. The combination Aller T4-T5 elicited reactions in 6 volunteers at the highest concentration (Table II B) therefore confirming its low but significant ability to bind IgE observed in competition ELISA.

TABLE II B

Below threshold (dubious) Skin prick
Reactivity lower than defined threshold:

| | Dilutions | | |
|---|---|---|---|
| | 1:1 | 1:10 | 1:100 |
| AllerT1 (10 µM) | 2 | 0 | 0 |
| AllerT2 (10 µM) | 0 | 0 | 0 |
| AllerT3 (10 µM) | 0 | 1 | 0 |
| Mix AllerT1-3 (10 µM) | 0 | 0 | 0 |
| AllerT4 (10 µM) | 0 | 0 | 1 |
| AllerT5 (10 µM) | 1 | 0 | 0 |
| Mix AllerT4-5 (10 µM) | 6 | 0 | 1 |

Toxicology Study in Mice

Contiguous overlapping peptides (COPs) have shown an excellent safety in bee venom allergic patients (Fellrath et al., J. Allergy Clin. Immunol, 111:854-861 (2003)). Immunological responses resembled those obtained when applying SIT, indicating, but not proving, a possible efficacy. Application of the same approach to birch pollen allergy is presented here. Surprisingly, one set of COPs derived from the Bet v 1 sequence showed residual IgE binding. Since the peptides composing this set, namely AllerT4 and AllerT5, themselves do not show such binding, an interaction of the two peptides in solution is the most probable cause of the appearance of a B cell epitope recognized by IgE. Such residual binding was observed in competition assays with sera from two patients as well as on 6 volunteers tested by prick tests. Whether mixing AllerT4-T5 results in few molecules with the original Bet v 1 conformation or whether the reconstructed B cell epitope is partially recognized by IgE with low affinity remains to be shown. The two sets of COPs combining Aller T1, T2 and T3 on one side and AllerT6, T7 and T8 on the other side, show no detectable IgE binding using either competition ELISA, degranulation assays or skin prick tests. It can therefore be expected that the combination of AllerT1, T2 and T3, named AllerT, will not elicit IgE mediated allergic responses in human.

A regulatory toxicology testing was performed in mice by the CERB (France) in order to prepare for the clinical trial in human. The study involved 40 animals divided in 2 groups of 10 males and 10 females, one dosed with the vehicle, namely Aluminium hydroxide, and the other dosed with AllerT (an equimolar mixture of AllerT1, AllerT2 and AllerT3 COPs) at 40 µg/animal. Allocation of each animal to the treatment was randomly determined before the start of the study. Homogeneity of the groups was validated on the criterion of body weight measured on the day of randomization, separately for males and females. The dose of 40 µg per animal corresponds to a quarter of the maintenance dose expected to be used in human (160 µg). AllerT or its vehicle was administered on days 1, 4, 8, 12 and 26 at approximately the same period of the day, by the subcutaneous route. For each administration, 200 µl of AllerT or vehicle was administered per animal. No mortality was observed in animals dosed either with the vehicle or with AllerT. No change in food consumption or body weight was noted.

During the general observations, no clinical sign was noted in animals dosed with the vehicle or with AllerT. No effect on the hematology and coagulation parameters was noted in mice dosed with AllerT, when compared to the vehicle group. No effect either on clinical chemistry parameters or on urinalysis was noted in animals dosed with AllerT, whatever the sex. No abnormality attributed to the vehicle or to AllerT was noticed in organs examined at necropsy. Therefore no mortality was attributed to the treatment with AllerT at 40 µg/animal, under the experimental conditions adopted, and no toxicity sign was noted. Except for histological changes at the site of injection due to the use of the adjuvant Aluminium hydroxide, no anatomical and histological changes were observed in organs prone to be the target of treatments with peptides or recombinant products. A limited immunogenicity test showed that, as expected, Aller T injection induced both specific IgG, including IgG2, in mice.

Treatment of Human Subjects with AllerT in a Clinical Trial Phase I/IIa

A single center, randomized, placebo-controlled phase I/IIa clinical trial was conducted in Lausanne (Switzerland) including volunteers with birch pollen allergic rhinitis and asthma to evaluate the safety, immunogenicity and potential efficacy of AllerT, based on contiguous overlapping peptides (COPs) derived from Bet v 1, the major birch pollen allergen. Prior to pollen season, AllerT in the adjuvant Aluminium Hydroxide was injected subcutaneously to 15 adult volunteers (18-45 years old) at day 0, day 7, day 14, day 21 and day 51. Control volunteers (n=5) received solely Aluminium Hydroxide as placebo. Immunological endpoints and/or biological safety tests were performed after each visit up to one month after treatment. During the birch pollen season 2009, volunteers were evaluated on the basis of the 32-items Rhinitis and Quality of Life Questionnaire (MiniRQLQ) and on asthma symptoms.

Overall AllerT was safe and all subjects completed the injection protocol. Local adverse events were mild and did not differ from placebo. No serious adverse events, no immediate allergic reactions and no AllerT-related clinically significant abnormal lab values were reported. In the active group, AllerT induced a vigorous early Bet v 1-specific cellular immune response marked by vaccine associated INF-gamma and over 5 fold increase in IL-10 secretion as judged on PBMCs (FIG. 5). This contributed to an at least 10 fold increase in anti-Bet v 1-specific IgG4 level increase (FIG. 6) whereas IgE response was limited. During seasonal exposure, an overall marked improvement in MiniRQLQ and asthma symptom score was observed as compared to placebo. Thus, immunotherapy with a mixture of three COPs derived from Bet v 1 (AllerT) was safe and immunogenic in volunteers with birch pollen allergic rhinitis and asthma, and led to a marked improvement of seasonal symptoms and quality of life (FIG. 7).

From these experiments it can be concluded that Aller T, a combination of the three peptides Aller T1, T2 and T3, represents a better candidate for the treatment of birch pollen allergy than the combination of Aller T4 and T5. Also contemplated are homologs of the Aller T1, T2 and T3 COPs, by amino acid changes within each peptide to produce homologs thereof wherein the reactivity of the homologs to IgE antibodies of patients who are allergic to birch pollen is eliminated while that with the T lymphocytes is still retained. Further contemplated are homologs of the COPs by shifting the limits of the COPs within the birch pollen major allergen Bet v1. Such homologs will result in products with equivalent profiles of non detectable IgE binding and T lymphocyte activity. Such products will present the same potential for safety and efficacy in human as Aller T and can be considered as equivalent in terms of chances for treatment, unless shown otherwise. Suitable homologs characterized by no reactivity to anti birch pollen IgE antibodies while maintaining reactivity to T lymphocytes may be identified by the methods described herein.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed is:

1. A composition comprising a plurality of contiguous overlapping peptide fragments comprising a first peptide consisting of the sequence from amino acid 2 to amino acids 42-52 of SEQ ID NO: 9 wherein the reactivity of said first peptide to IgE antibodies of subjects who are allergic to birch pollen is eliminated while the reactivity with the T lymphocytes from subjects who are allergic to birch pollen is retained; a second polypeptide consisting of the sequence from amino acids 42-52 to amino acids 96-131 of SEQ ID NO: 9 wherein the reactivity of said second peptide to IgE antibodies of subjects who are allergic to birch pollen is eliminated while the reactivity with the T lymphocytes from subjects who are allergic to birch pollen is retained and a third peptide consisting of the sequence from amino acids 96-131 to amino acid 160 of SEQ ID NO: 9 wherein the reactivity of said third peptide to IgE antibodies of subjects who are allergic to birch pollen is eliminated while the reactivity with the T lymphocytes from subjects who are allergic to birch pollen is retained.

2. The composition of claim 1 wherein the first and second peptides overlap each other by 1 to 11 amino acids.

3. The composition of claim 1 wherein the second and third peptides overlap each other by 5 to 20 amino acids.

4. The composition of claim 1 comprising a combination of the first peptide having SEQ ID NO: 1, the second peptide having SEQ ID NO:2 and the third peptide having SEQ ID NO: 3.

5. The composition of claim 1 comprising a combination of the first peptide having SEQ ID NO: 6, the second peptide having SEQ ID NO: 7 and the third peptide having SEQ ID NO: 8.

6. A peptide consisting of the sequence from amino acid 2 to amino acids 42-52 of SEQ ID NO: 9 wherein the reactivity of said peptide to IgE antibodies of subjects who are allergic to birch pollen is eliminated while the reactivity with the T lymphocytes from subjects who are allergic to birch pollen is retained.

7. The peptide of claim 6 which has the sequence of SEQ ID NO: 1.

8. The peptide of claim 6 which has the sequence of SEQ ID NO 6.

9. A peptide consisting of the sequence from amino acids 42-52 to amino acids 96-131 of SEQ ID NO: 9 wherein the reactivity of said peptide to IgE antibodies of subjects who are allergic to birch pollen is eliminated while the reactivity with the T lymphocytes from subjects who are allergic to birch pollen is retained.

10. The peptide of claim 9 which has the sequence of SEQ ID NO: 2.

11. The peptide of claim 9 which has the sequence of SEQ ID NO 7.

12. A peptide consisting of the sequence from amino acids 96-131 to amino acid 160 of SEQ ID NO: 9 wherein the reactivity of said peptide to IgE antibodies of subjects who are allergic to birch pollen is eliminated while the reactivity with the T lymphocytes from subjects who are allergic to birch pollen is retained.

13. The peptide of claim 12 which has the sequence of SEQ ID NO: 3.

14. The peptide of claim 12 which has the sequence SEQ ID NO 8.

15. The composition of anyone of claim 1 or 6 which is provided in dry powdered form.

16. The composition of anyone of claim 1 or 6 further comprising a pharmaceutically acceptable carrier or diluent.

17. The composition of claim 16 further comprising an adjuvant.

18. The composition of claim 17 wherein the adjuvant is aluminium hydroxide.

19. A method of specific immunotherapy against birch pollen allergies comprising administering to a patient in need thereof one or more allergens selected from the group consisting of a first peptide consisting of the sequence from amino acid 2 to amino acids 42-52 of SEQ ID NO: 9 wherein the reactivity of said first peptide to IgE antibodies of subjects who are allergic to birch pollen is eliminated while the reactivity with the T lymphocytes from subjects who are allergic to birch pollen is retained; a second polypeptide consisting of the sequence from amino acids 42-52 to amino acids 96-131 of SEQ ID NO: 9 wherein the reactivity of said second peptide to IgE antibodies of subjects who are allergic to birch pollen is eliminated while the reactivity with the T lymphocytes from subjects who are allergic to birch pollen is retained and a third peptide consisting of the sequence from amino acids 96-131 to amino acid 160 of SEQ ID NO: 9 wherein the reactivity of said third peptide to IgE antibodies of subjects who are allergic to birch pollen is eliminated while the reactivity with the T lymphocytes from subjects who are allergic to birch pollen is retained.

20. The method of claim 19 wherein the peptides are administered using intradermal injection, subcutaneous injection, intramuscular injection, intravenous injection, transdermal, intranasal, oral, sublingual, intraocular, or intrathecal techniques.

21. The method of claim 19 wherein the patient is treated with the combination of each of a first peptide consisting of the sequence from amino acid 2 to amino acids 42-52 of SEQ ID NO: 9 wherein the reactivity of said first peptide to IgE antibodies of subjects who are allergic to birch pollen is eliminated while the reactivity with the T lymphocytes from subjects who are allergic to birch pollen is retained; a second peptide consisting of the sequence from amino acids 42-52 to amino acids 96-131 of SEQ ID NO: 9 wherein the reactivity of said second peptide to IgE antibodies of subjects who are allergic to birch pollen is eliminated while the reactivity with the T lymphocytes from subjects who are allergic to birch pollen is retained and a third peptide consisting of the sequence from amino acids 96-131 to amino acid 160 of SEQ ID NO: 9 wherein the reactivity of said third peptide to IgE antibodies of subjects who are allergic to birch pollen is eliminated while the reactivity with the T lymphocytes from subjects who are allergic to birch pollen is retained.

22. The method of claim 19 wherein the first and second peptides overlap each other by at least 1 to 11 amino acids.

23. The method of claim 19 wherein the second and third peptides overlap each other by at least 5-20 amino acids.

24. The method of claim 19 wherein the first peptide consists of SEQ ID NO: 1, the second peptide consists of SEQ ID NO:2 and the third peptide consists of SEQ ID NO: 3.

25. The method of claim 19 wherein the first peptide consists of SEQ ID NO: 6, the second peptide consists of SEQ ID NO:7 and the third peptide consists of SEQ ID NO: 8.

* * * * *

SEQUENCE LISTING

```
<160> NUMBER OF SEQ ID NOS: 10

<210> SEQ ID NO 1
<211> LENGTH: 49
<212> TYPE: PRT
<213> ORGANISM: Artificial Sequence
<220> FEATURE:
<223> OTHER INFORMATION: Synthetic peptide

<400> SEQUENCE: 1

Gly Val Phe Asn Tyr Glu Thr Glu Thr Thr Ser Val Ile Pro Ala Ala
1               5                  10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly

<210> SEQ ID NO 2
<211> LENGTH: 71
<212> TYPE: PRT
<213> ORGANISM: Artificial Sequence
<220> FEATURE:
<223> OTHER INFORMATION: Synthetic peptide

<400> SEQUENCE: 2

Asn Gly Gly Pro Gly Thr Ile Lys Lys Ile Ser Phe Pro Glu Gly Phe
1               5                  10                  15

Pro Phe Lys Tyr Val Lys Asp Arg Val Asp Glu Val Asp His Thr Asn
            20                  25                  30

Phe Lys Tyr Asn Tyr Ser Val Ile Glu Gly Gly Pro Ile Gly Asp Thr
        35                  40                  45

Leu Glu Lys Ile Ser Asn Glu Ile Lys Ile Val Ala Thr Pro Asp Gly
    50                  55                  60

Gly Ser Ile Leu Lys Ile Ser
65                  70
```

```
<210> SEQ ID NO 3
<211> LENGTH: 55
<212> TYPE: PRT
<213> ORGANISM: Artificial Sequence
<220> FEATURE:
<223> OTHER INFORMATION: Synthetic peptide

<400> SEQUENCE: 3

Val Ala Thr Pro Asp Gly Gly Ser Ile Leu Lys Ile Ser Asn Lys Tyr
1               5                   10                  15

His Thr Lys Gly Asp His Glu Val Lys Ala Glu Gln Val Lys Ala Ser
            20                  25                  30

Lys Glu Met Gly Glu Thr Leu Leu Arg Ala Val Glu Ser Tyr Leu Leu
        35                  40                  45

Ala His Ser Asp Ala Tyr Asn
    50                  55

<210> SEQ ID NO 4
<211> LENGTH: 84
<212> TYPE: PRT
<213> ORGANISM: Artificial Sequence
<220> FEATURE:
<223> OTHER INFORMATION: Synthetic peptide

<400> SEQUENCE: 4

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser

<210> SEQ ID NO 5
<211> LENGTH: 96
<212> TYPE: PRT
<213> ORGANISM: Artificial Sequence
<220> FEATURE:
<223> OTHER INFORMATION: Synthetic peptide

<400> SEQUENCE: 5

Phe Lys Tyr Val Lys Asp Arg Val Asp Glu Val Asp His Thr Asn Phe
1               5                   10                  15

Lys Tyr Asn Tyr Ser Val Ile Glu Gly Gly Pro Ile Gly Asp Thr Leu
            20                  25                  30

Glu Lys Ile Ser Asn Glu Ile Lys Ile Val Ala Thr Pro Asp Gly Gly
        35                  40                  45

Ser Ile Leu Lys Ile Ser Asn Lys Tyr His Thr Lys Gly Asp His Glu
    50                  55                  60

Val Lys Ala Glu Gln Val Lys Ala Ser Lys Glu Met Gly Glu Thr Leu
65                  70                  75                  80

Leu Arg Ala Val Glu Ser Tyr Leu Leu Ala His Ser Asp Ala Tyr Asn
                85                  90                  95

<210> SEQ ID NO 6
```

<211> LENGTH: 48
<212> TYPE: PRT
<213> ORGANISM: Artificial Sequence
<220> FEATURE:
<223> OTHER INFORMATION: Synthetic peptide

<400> SEQUENCE: 6

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

<210> SEQ ID NO 7
<211> LENGTH: 75
<212> TYPE: PRT
<213> ORGANISM: Artificial Sequence
<220> FEATURE:
<223> OTHER INFORMATION: Synthetic peptide

<400> SEQUENCE: 7

Asn Ile Glu Gly Asn Gly Gly Pro Gly Thr Ile Lys Lys Ile Ser Phe
1               5                   10                  15

Pro Glu Gly Phe Pro Phe Lys Tyr Val Lys Asp Arg Val Asp Glu Val
            20                  25                  30

Asp His Thr Asn Phe Lys Tyr Asn Tyr Ser Val Ile Glu Gly Gly Pro
        35                  40                  45

Ile Gly Asp Thr Leu Glu Lys Ile Ser Asn Glu Ile Lys Ile Val Ala
    50                  55                  60

Thr Pro Asp Gly Gly Ser Ile Leu Lys Ile Ser
65                  70                  75

<210> SEQ ID NO 8
<211> LENGTH: 58
<212> TYPE: PRT
<213> ORGANISM: Artificial Sequence
<220> FEATURE:
<223> OTHER INFORMATION: Synthetic peptide

<400> SEQUENCE: 8

Ile Lys Ile Val Ala Thr Pro Asp Gly Gly Ser Ile Leu Lys Ile Ser
1               5                   10                  15

Asn Lys Tyr His Thr Lys Gly Asp His Glu Val Lys Ala Glu Gln Val
            20                  25                  30

Lys Ala Ser Lys Glu Met Gly Glu Thr Leu Leu Arg Ala Val Glu Ser
        35                  40                  45

Tyr Leu Leu Ala His Ser Asp Ala Tyr Asn
    50                  55

<210> SEQ ID NO 9
<211> LENGTH: 160
<212> TYPE: PRT
<213> ORGANISM: Artificial Sequence
<220> FEATURE:
<223> OTHER INFORMATION: Synthetic peptide

<400> SEQUENCE: 9

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
            20                  25                  30

-continued

```
Lys Val Ala Pro Gln Ala Ile Ser Ser Val Glu Asn Ile Glu Gly Asn
         35                  40                  45

Gly Gly Pro Gly Thr Ile Lys Lys Ile Ser Phe Pro Glu Gly Phe Pro
     50                  55                  60

Phe Lys Tyr Val Lys Asp Arg Val Asp Glu Val Asp His Thr Asn Phe
65                   70                  75                  80

Lys Tyr Asn Tyr Ser Val Ile Glu Gly Gly Pro Ile Gly Asp Thr Leu
                 85                  90                  95

Glu Lys Ile Ser Asn Glu Ile Lys Ile Val Ala Thr Pro Asp Gly Gly
             100                 105                 110

Ser Ile Leu Lys Ile Ser Asn Lys Tyr His Thr Lys Gly Asp His Glu
             115                 120                 125

Val Lys Ala Glu Gln Val Lys Ala Ser Lys Glu Met Gly Glu Thr Leu
         130                 135                 140

Leu Arg Ala Val Glu Ser Tyr Leu Leu Ala His Ser Asp Ala Tyr Asn
145                 150                 155                 160

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 10

Gly Xaa Gly Xaa Xaa Gly
1               5
```